United States Patent [19]

Elstner et al.

[11] Patent Number: 4,666,832
[45] Date of Patent: May 19, 1987

[54] PYRUVATE OXIDASE

[75] Inventors: Erich Elstner, Gröbenzell; Karl-Heinz Schleifer, Unterschleissheim; Friedrich Götz, Augsburg; Barbara Sedewitz, Munich; Albert Röder, Seeshaupt; Hans Möllering; Hans Seidel, both of Tutzing, all of Fed. Rep. of Germany

[73] Assignee: Boehringer Mannheim GmbH, Mannheim, Fed. Rep. of Germany

[21] Appl. No.: 583,728

[22] Filed: Feb. 27, 1984

[30] Foreign Application Priority Data

Feb. 25, 1983 [DE] Fed. Rep. of Germany ....... 3306719

[51] Int. Cl.$^4$ .............................................. C12Q 1/26
[52] U.S. Cl. ...................................... 435/25; 435/28; 435/183; 435/189; 435/853; 435/885
[58] Field of Search .................... 435/25, 28, 183, 189

[56] References Cited

U.S. PATENT DOCUMENTS 4,246,342  1/1981  Misaki et al. ........................ 435/16

OTHER PUBLICATIONS

Gotz et al.—Arch. Microbiology vol. 125 (1980) pp. 209-214.
Yamanaka—Chem. Absts. vol. 52, No. 22, 25 Nov. 1958 (20374h) (20375b).
Scardovi—Chem. Absts. vol 57, No. 13, 24 (17176f).
Goetz—Chem. Absts. vol. 92, No. 25, 23 (211562x).
Hakko—Chem. Absts. vol. 102, No. 3 (22815w).

Primary Examiner—Sam Rosen
Attorney, Agent, or Firm—Felfe & Lynch

[57] ABSTRACT

The present invention provides a new pyruvate oxidase which decarboxylates pyruvate with the formation of hydrogen peroxide, characterized in that it is active without the addition of FAD, TPP and divalent metal ions.

The present invention also provides a process for preparing this new enzyme and a reagent containing it.

10 Claims, No Drawings

PYRUVATE OXIDASE

The present invention is concerned with new pyruvate oxidase, with a process for its preparation and with the use thereof.

Pyruvate oxidase (E.C. 1.2.3.3) is an enzyme which decarboxylates pyruvate in the presence of phosphate ions and oxygen with the formation of hydrogen peroxide (Federation Proceedings, 13 (1954) 734–738). Of the reaction products obtained, i.e. acetyl phosphate, carbon dioxide and hydrogen peroxide, the latter is especially readily detectable analytically and, therefore, this enzyme can be used for the quantitative determination of pyruvate and of pyruvate-forming enzymes and of their substrates.

A characteristic property of the known pyruvate oxidase is that for activity it needs an addition of FAD (flavine-adenine-dinucleotide), TPP (thiamine pyrophosphate) and of divalent metal ions. However, this property can have a disturbing influence on a process or reagent for the determination of pyruvate or pyruvate-forming reactions. Thus, especially TPP tends, in the presence of serum and of magnesium ions, to give rise to the formation of insoluble precipitates which bring about turbidities and, therefore, impair optical measurements. Furthermore, the storage stability of TPP in a combined reagent, especially in the presence of divalent metal ions, is reduced so that in the course of storage it gradually decomposes. This latter property is especially disturbing in the scope of a kinetic wet test. Therefore, it would be very desirable to have available, for the determination of pyruvate and for a reagent suitable herefor, a pyruvate oxidase which is independent of the above-mentioned substances and especially of TPP and divalent metal ions, i.e. also displays a sufficiently high activity without the addition thereof.

Surprisingly, we have now found, and upon this is based the present invention, that a pyruvate oxidase exists which is active without the addition of FAD, TPP and divalent metal ions.

Therefore, according to the present invention, there is provided a pyruvate oxidase which decarboxylates pyruvate with the formation of hydrogen peroxide which is characterised in that it is active without the addition of FAD, TPP and divalent metal ions.

However, the pyruvate oxidase according to the present invention also differs in its other properties, in some cases considerably, from the known pyruvate oxidase, such as is described, for example, in Federal Republic of Germany Patent Specification No. 29 11 481. In particular, the optimum pH range for the activity of the enzyme according to the present invention is lower (pH 5.0 to 6.5, optimum 5.7) than in the case of the known enzyme (pH 6.5 to 7.5), the molecular weight of the enzyme according to the present invention is lower (146,000, determined in the ultracentrifuge) than that of the known enzyme (190,000, determined by gelfiltration with Sephadex G 200) and, which is expecially important for use for pyruvate determination, the Michaelis constant $K_M$ for pyruvate is more than a power of ten lower. In the following, there are compared properties of the enzyme according to the present invention with properties of the known enzyme:

| property | enzyme according to the present invention | pyruvate oxidase according to Federal Republic of Germany Patent Specification No. 2911481 |
|---|---|---|
| $K_M$ pyruvate (25° C.) | 0.4 mmol/l. | 10.2 mmol/l. |
| $K_M$ phosphate (25° C.) | 2.3 mmol/l. | 0.96 mmol/l. |
| stability optimum | pH 5.6 to 5.8 | pH 6.5 to 7.5 |

| Substrate specificity: | | |
|---|---|---|
| substrate | enzyme according to the present invention | pyruvate oxidase according to Federal Republic of Germany Patent Specification No. 2911481 |
| pyruvate | 100% | 100% |
| α-ketobutyrate | 0% | 3% |
| acetaldehyde | 15% | 0% |
| methylglyoxal | 20% | 0% |

The following Table 1 shows the influence of inhibitors in comparison with the known enzyme:

TABLE 1

| inhibitor | concentration in mmol/l. | activity in % of pyruvate oxidase according to Fed. Rep. of Germany Pat. Specn. No. 2911481 | activity in % of pyruvate oxidase according to present invention |
|---|---|---|---|
| without | 0 | 100 | 100 |
| KCN | 10 | 85 | 75 |
|  | 100 | 0 | 5 |
| NaN$_3$ | 100 | 75 | 62 |
| EDTA | 0.01 | 78 | 100 |
|  | 0.1 | 30 | 100 |
|  | 1 | 7 | 98 |
|  | 10 | 0 | 85 |

The following Table 2 shows the influence of activators in comparison with the known enzyme:

TABLE 2

| activator | concentration in mmol/l. | activity in % of pyruvate oxidase according to Fed. Rep. of Germany Pat. Specn. No. 2911481 | activity in % of pyruvate oxidase according to present invention |
|---|---|---|---|
| thiamine-PP + MnSO$_4$ | 0.2 1 | 100 | 100 |
| 0 | 0 | 0.2 | 84 |
| CoCl$_2$ | 1 | 0 | 97 |
| MgSO$_4$ | 0.1 | 0.2 | 97 |
| MnSO$_4$ | 0.1 | 13 | 97 |
| thiamine-PP | 0.2 | 46 | 97 |
| FAD | 0.1 | 0 | 93 |
| FAD + TPP | 0.4 + 0.2 | 61 | 93 |
| MgSO$_4$ + TPP | 0.4 + 0.2 | 55 | 100 |

The above values show that the inhibiting action of ethylenediamine-tetraacetic acid (EDTA) on the enzyme according to the present invention is about a thousand times weaker than in the case of the known enzyme and, after several days dialysis of the enzyme according to the present invention, the addition of TPP, FAD and Mn$^{2+}$ only increases the activity by 5 to 15%, whereas the known enzyme is not active without these activators.

In the Ouchterlony test (rabbit), no immunological cross-reactions take place between the enzyme according to the present invention and the known enzyme.

The enzyme according to the present invention is obtained from micro-organisms which contain an amount of the enzyme making working up worthwhile, using the usual biochemical methods. For each enrichment step, on the basis of the characteristic properties of the enzyme, namely hydrogen peroxide formation from pyruvate in the absence of FAD, TPP and divalent metal ions, it can easily be determined in which fraction the desired enzyme is present. Preferably, the aqueous micro-organism digest is mixed directly or after separation of insolubles with polyethyleneimine and the insolubles hereby formed are separated off.

The preferred sources for the enzyme according to the present invention are lactic acid bacteria. Having regard to their content of the desired enzyme, *Lactobacillus plantarum* DSM 2571, *Lactobacillus salivarius* DSM 2573, *Leuconostoc mesenteroides* DSM 2572 and/or *Streptococcus cremoris* DSM 2574 are especially preferred sources. In the course of the investigation of several hundred different lactic acid bacteria, the enzyme according to the present invention was detected in about one quarter of the investigated strains. From this it can be concluded that the enzyme is widely distributed. Furthermore, there are indications for the belief that it is also to be found in micro-organisms which do not belong to the lactic acid bacteria.

In order to obtain the enzyme from the microorganisms, the latter are digested by conventional methods. Good results were achieved with the use of ultrasonics and of a Dyno-mill (glass pearls). Digestion by high pressure dispersion also gave good results. In general, however, other digestion methods, such as are described, for example, in Federal Republic of German Patent Specification No. 29 11 481, can also be used.

The enrichment and purification of the enzyme according to the present invention can, as already mentioned, be achieved in various ways by conventional biochemical methods. According to one investigated method of working, after digestion insolubles are centrifuged off, the supernatant is fractionated between 25 and 65% ammonium sulphate at pH 6.3, the active fraction is chromatographed over dextran blue Sepharose (Pharmacia, Upsala, Sweden), the active fraction is again fractionated with ammonium sulphate between 20 and 30% saturation and finally purified by passage through a molecular sieve (Sephadex 34 of the firm LKB).

In an alternative method, the digest liquid was mixed with 4% polyethyleneimine, the precipitate is removed and an ammonium sulphate precipitation is carried out in the supernatant at 65% saturation. The precipitate is collected and, after dialysis, subjected to a saccharose gradient step. After further ammonium sulphate precipitation up to 65% and gel filtration, a high purification is carried out over dextran blue Sepharose.

By means of the described processes, an approximately 20 to 30 fold enrichment can be achieved up to a specific activity of about 6 to 9 U/mg. protein.

According to a further aspect of the present invention, the new enzyme is used for the determination of pyruvate by the measurement of hydrogen peroxide formed. For this purpose, numerous appropriate methods are known which do not have to be here specially described. The measurement of the oxygen consumption, for example by means of oxygen electrodes, can also be used.

The enzyme according to the present invention can be used not only for the determination of pyruvate per se but especially also in the determination of substrates and enzymes which lead to a pyruvate formation.

Typical examples of determinations which can be carried out with the enzyme according to the present invention include: glutamate-pyruvate-transaminase or α-ketoglutarate; glutamate-oxalacetate-transaminase; pyruvate kinase or ADP; lactate dehydrogenase or lactic acid; glycerol or glycerophosphate-kinase; triglyceride; creatine phosphokinase or creatine; and myokinase, thiokinase or fatty acid.

The present invention also provides a reagent for the determination of pyruvate, which contains the pyruvate oxidase according to the present invention, phosphate, buffer, a system for the determination of hydrogen peroxide and possibly a system for the formation of pyruvate.

The buffer used can be any appropriate buffer substance which buffers in the above-mentioned pH range in which the enzyme is active and stable. Phosphate buffer is also suitable so that a special addition of buffer in addition to the phosphate necessary for the reaction is no longer necessary. However, with regard to the choice of the buffer, account must also be taken of the pH values which are to be present for the adjuvant enzymes in the system for the determination of hydrogen peroxide or in the system for the formation of pyruvate. On the basis of the known data of these enzymes, there is no difficulty in making an appropriate choice of buffer.

The reagent according to the present invention can readily be used for the impregnation of carrier materials, such as paper, synthetic resin film and the like, to make test strips.

The reagent according to the present invention preferably contains 1 to 50 U/ml. pyruvate oxidase, 10 to 500 mmol/liter phosphate, buffer pH 6 to 8 (possibly 1 to 50 mmol/liter of substrate, for example for GPT measurement of each of α-ketoglutarate and 1-alanine) and, as system for the determination of hydrogen peroxide, 0.5 to 40 mmol/liter 4-aminoantipyrine, 1 to 50 mmol/liter 2-hydroxy-3,5-dichlorobenzenesulphonic acid (HDBA) and 0.2 to 20 U/ml. peroxidase.

The present invention overcomes the disadvantages of the known enzyme and provides the possibility of preparing a reagent with superior storage stability.

The following examples are given for the purpose of illustrating the present invention:

EXAMPLE 1

Isolation of Pyruvate Oxidase (Py-OD) from *Lactobacillus plantarum* DSM 2571

1. Culturing

Culture medium: per liter: 10 g. Bacto-Trypton/Oxoid; 4 g. yeast extract Oxoid; 2 g. $K_2HPO_4 \times 3H_2O$; 2 g. diammonium hydrogen citrate; 1 ml. Tween (polyoxyethylenesorbitan monooleate); 0.2 g. $MgSO_4 \times 7H_2O$; 0.2 g. $MnSO_4 \times H_2O$; 0.02 g. molybdanum sulphide; 10 g. lactose; and 3.2 g. pyruvic acid; pH 7.

150 ml. of medium are inoculated by stab cultures of the composition as above or the MRS+ medium usual for lactic acid bacteria and shaken at 28° C. After growth has taken place, 150 ml. of medium (see above)

are again inoculated with 15% of the grown culture and shaken in a 500 ml. Erlenmeyer flask at 28° C. up to the conclusion of the late log phase.

+MRS medium has the following composition: per liter: 2 g. meat extract (Merck); 10 g. peptone from casein, tryptic; 4 g. yeast extract; 20 g. glucose; 1 ml. Tween 80; 2.5 g. $K_2HPO_4 \times 3H_2O$; 5 g. Na acetate $\times 3$-$H_2O$; 2 g. diammonium citrate; 200 mg. $MgSO_4 \times 7H_2O$; and 50 mg. $MnSO_4 \times H_2O$.

2. Isolation

From a 50 liter culture of *Lactobacillus pl.* DSM 2571 containing 120 U/liter Py-OD, there were harvested 300 g. of moist mass by centrifuging. 100 g. of cells are digested in a glass Dynomill and, after the addition of 4% polyethyleneimine, are centrifuged and the supernatant further worked up via the steps of ammonium sulphate (AS) (25 to 65%) fractionation at pH 6.3, dextran blue Sepharose chromatography (Pharmacia), a second ammonium sulphate (AS) fractionation between 20 and 30% and passage over a molecular sieve Sephadex ACA 34. (Firm LKB).

The data of the enrichment steps are summarised in the following Table:

| step | vol. (ml.) | units | protein (mg.) | specific activity | yield % |
|---|---|---|---|---|---|
| digest supernatant | 480 | 2516 | 6700 | 0.37 | 100 |
| 1st AS fractionation | 98 | 2436 | 5540 | 0.44 | 97 |
| dextran blue Sepharose | 54 | 2284 | 2560 | 0.89 | 91 |
| 2nd AS fractionation | 13 | 748 | 753 | 1.0 | 30 |
| ACA 34 mol. sieve | 30 | 590 | 102 | 5.8 | 23.5 |

The purified enzyme has a specific activity of 5.8 U/mg. and contains less than 0.03% Apo-glutamatepyruvate-transaminase+α-ketoglutarate-oxidase, as well as less than 0.002% NADH-oxidase.

The activity of the pyruvate oxidase was determined under the following conditions:

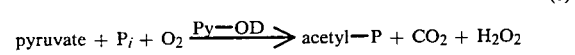

pyruvate + $P_i$ + $O_2$ $\xrightarrow{Py-OD}$ acetyl—P + $CO_2$ + $H_2O_2$    (1)

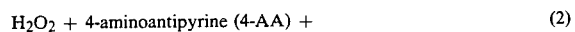

$H_2O_2$ + 4-aminoantipyrine (4-AA) +    (2)

2-hydroxy-3,5-dichlorobenzenesulphonic acid (HDBA) $\xrightarrow{POD}$

quinone coloured material (546 nm) + $2H_2O$

Hydrogen peroxide is consumed in an amount which is equimolar to the amount of coloured material formed.

1 Unit Py-OD=1 μmol pyruvate conversion/min. at 25° C.

Determination of Pyruvate 72 mM potassium phosphate buffer, pH 6.7; 8 mM 4-AA; 6.8 mmol/liter HDBA; 0.01 mmol/liter FAD; 2 U POD; and 10 U Py-OD per ml. The start for an end value reaction takes place by the addition of 0.05 μmol pyruvate or pyruvate-containing sample in a cuvette volume of 2 ml. at 1 cm. layer thickness and at 37° C. The reaction comes to a stop after 15 minutes. An extinction coefficient at 546 nm of $\epsilon = 16.5$ $cm^2/\mu mol$ was measured for purest pyruvate (monosodium salt).

EXAMPLE 2

Kinetic Determination of GPT

To 2.5 ml. of a solution containing 80 mmol/liter pH 6.7 $KH_2PO_4$, 800 mmol/liter alanine, 0.2 mmol/liter N-(3'-sulphonyl-4'-hydroxy-5'-chlorophenyl)-4-aminoantipyrine, 18 mmol/liter α-ketoglutaric acid, 0.2 U/ml. pyruvate oxidase and 2 U/ml. POD is added 0.1 ml. of sample. After 3 minutes, the extinction change per minute is determined. The measurement temperature is 25° C. and the measurement wavelength is 546 nm. $\epsilon$ is 19.6, the total volume is 2.6 ml. and the sample volume is 0.1 ml. The activity of the GPT is calculated from the extinction increase per minute.

EXAMPLE 3

Kinetic Determination of GOT

To a batch analogous to Example 2 but which, instead of alanine, contains 200 mmol/liter alanine-sulphinic acid and under the same conditions as in Example 2, there is added a GOT-containing sample. The content of GOT is calculated directly from the extinction change per minute.

EXAMPLE 4

Test Strips for GPT

For the preparation of test strips for GPT, 2 papers are impregnated:

(A) Enzyme paper 0.5 mol/liter morpholine-ethanesulphonic acid/potassium hydroxide, pH 6.5 (MOPS buffer)
800 mmol/liter alanine
1 mmol/liter potassium hydrogen phosphate
20,000 U/liter POD
200,000 U/liter pyruvate oxidase With this solution there is impregnated an absorbent paper with a thickness of 50 μm, a weight per unit surface area of 12 $g/m^2$ and an absorbancy of 50 g water/$m^2$, whereafter the paper is dried for 5 minutes at 30° C. (e.g. tea bag paper of the firm Schöller & Hösch). The paper is subsequently cut up into 1 cm wide strips.

(B) Indicator paper 10 mmol/liter 4,5-[4-dimethylaminophenyl]-2-(3,5-dimethoxy-4-hydroxyphenyl)-imidazole
18 mmol/liter α-ketoglutaric acid dissolved in
100 mmol/liter hydrogen chloride (buffer system).

With this solution there is also impregnated an appropriate absorbent paper which is then dried for 5 minutes at 30° C. and cut up into 1 cm wide strips. The material is worked up as follows: A 1 cm wide, transparent polycarbonate film of 100 μm thickness, together with the indicator paper and the enzyme paper, is applied to one side of a plastics strip with the help of a fixing means so that the foil comes to lie on the outside, the indicator paper in the middle and the enzyme paper on the inside. In addition, a 15 mm wide glass fibre fleece with a thickness of 1.5 mm and a fibre thickness of about 2 μm is applied so that the free end of the film and the impregnated papers still extend 6 mm over the fleece. It is then cut up into 6 mm wide test strips. If 15 μl of whole blood are now applied to the sample application zone, then, within 30 to 60 seconds, the plasma portion penetrates the whole of the glass fibre fleece even below the transparent film, whereas the erythrocytes are held in the sample application region. After applying pressure to the film, the enzyme and the indicator paper now come into contact with the developed plasma and are uniformly moistened through therewith. The GPT contained in the plasma reacts with a blue coloration, the intensity of which is proportional to the amount of GPT in the plasma portion and can possibly be measured in a remission photometer. Other sample materials, such as serum, plasma and the like, also react in the same way.

EXAMPLE 5

Test Strips for GOT

The test strips for GOT are prepared in completely the same way as the strips for GPT according to Example 4 except that in the test paper instead of alanine, there is present 200 mmol alaninesulphinic acid. The blue colour formed after applying pressure to the transparent film is a measure of the amount of GOT in the sample.

We claim:

1. A purified pyruvate oxidase which decarboxylates pyruvate with the formation of hydrogen peroxide, is active without the addition of FAD, TPP and divalent metal ions and has an activity optimum at pH 5.7.

2. Process for the preparation of the pyruvate oxidase according to claim 1 comprising the steps of digesting in an aqueous medium, a microorganism containing the pyruvate oxidase, mixing the aqueous digest with polyethyleneimine, separating off insolubles and separating and purifying the enzyme from the aqueous digestion solution.

3. Process according to claim 2, wherein the microorganisms used are lactic acid bacteria.

4. Process according to claim 3, wherein the lactic acid bacteria used are *Lactobacillus plantarum* DSM 2571, *Lactobacillus salivarius* DSM 2573, *Leuconostoc mesenteroides* DSM 2572 and/or *Streptococcus cremoris* DSM 2574.

5. In the method for the determination of pyruvate using pyruvate oxidase by the measurement of hydrogen peroxide formed or of oxygen consumed the improvement comprising using the pyruvate oxidase of claim 1.

6. Reagent for the determination of pyruvate, comprising pyruvate oxidase according to claim 1, phosphate, buffer and a system for the determination of hydrogen peroxide.

7. Reagent according to claim 6, in the form of a test strip.

8. Reagent according to claim 7, wherein the system for the determination of hydrogen peroxide contains peroxidase and for indicator 4-aminoantipyrine and 2-hydroxy-3,5-dichlorobenzenesulfonic acid.

9. Reagent according to claim 7, wherein the system for the hydrogen peroxide contains peroxidase and for indicator 4,5-(4-dimethyl aminophenyl)-2-(3,5-dimethoxy-4-hydroxyphenyl)-imidazole.

10. Reagent according to claim 7, consisting of a sandwich carrier, wherein one carrier contains the indicator and a further carrier contains the other compounds.

* * * * *